United States Patent [19]

Gupta

[11] Patent Number: 5,292,964
[45] Date of Patent: Mar. 8, 1994

[54] PREPARATION OF ALKYL TERTIARY BUTYL ETHER

[75] Inventor: Vijai P. Gupta, Berwyn, Pa.

[73] Assignee: Arco Chemical Technology, L.P., Wilmington, Del.

[21] Appl. No.: 976,800

[22] Filed: Nov. 16, 1992

[51] Int. Cl.$^5$ .................... C07L 41/09; C07C 41/06
[52] U.S. Cl. .................... 568/697; 568/698
[58] Field of Search .................... 568/698, 697

[56] References Cited

U.S. PATENT DOCUMENTS

| | | |
|---|---|---|
| 4,144,138 | 3/1979 | Rao et al. |
| 4,822,921 | 4/1989 | Knifton et al. |
| 4,918,244 | 4/1990 | Nelson et al. |
| 4,925,989 | 5/1990 | Hagan et al. |
| 5,099,072 | 3/1992 | Knifton |

FOREIGN PATENT DOCUMENTS

| | | |
|---|---|---|
| 0502265 | 9/1992 | European Pat. Off. |
| 0502651 | 9/1992 | European Pat. Off. |

*Primary Examiner*—Howard T. Mars
*Attorney, Agent, or Firm*—John C. Martin, Jr.

[57] ABSTRACT

The present invention provides a process for the preparation of MTBE or ETBE wherein TBA is reacted with methanol or ethanol and an effluent is formed which contains the water of etherification and at least 1 mol lower alcohol per 2 mols MTBE or ETBE, this effluent is distilled to separate an overhead of lower alcohol and ether from a bottoms containing the water of reaction, and a lower alcohol/ether admixture from the overhead is reacted with isobutylene to form additional quantities of MTBE or ETBE.

5 Claims, 1 Drawing Sheet

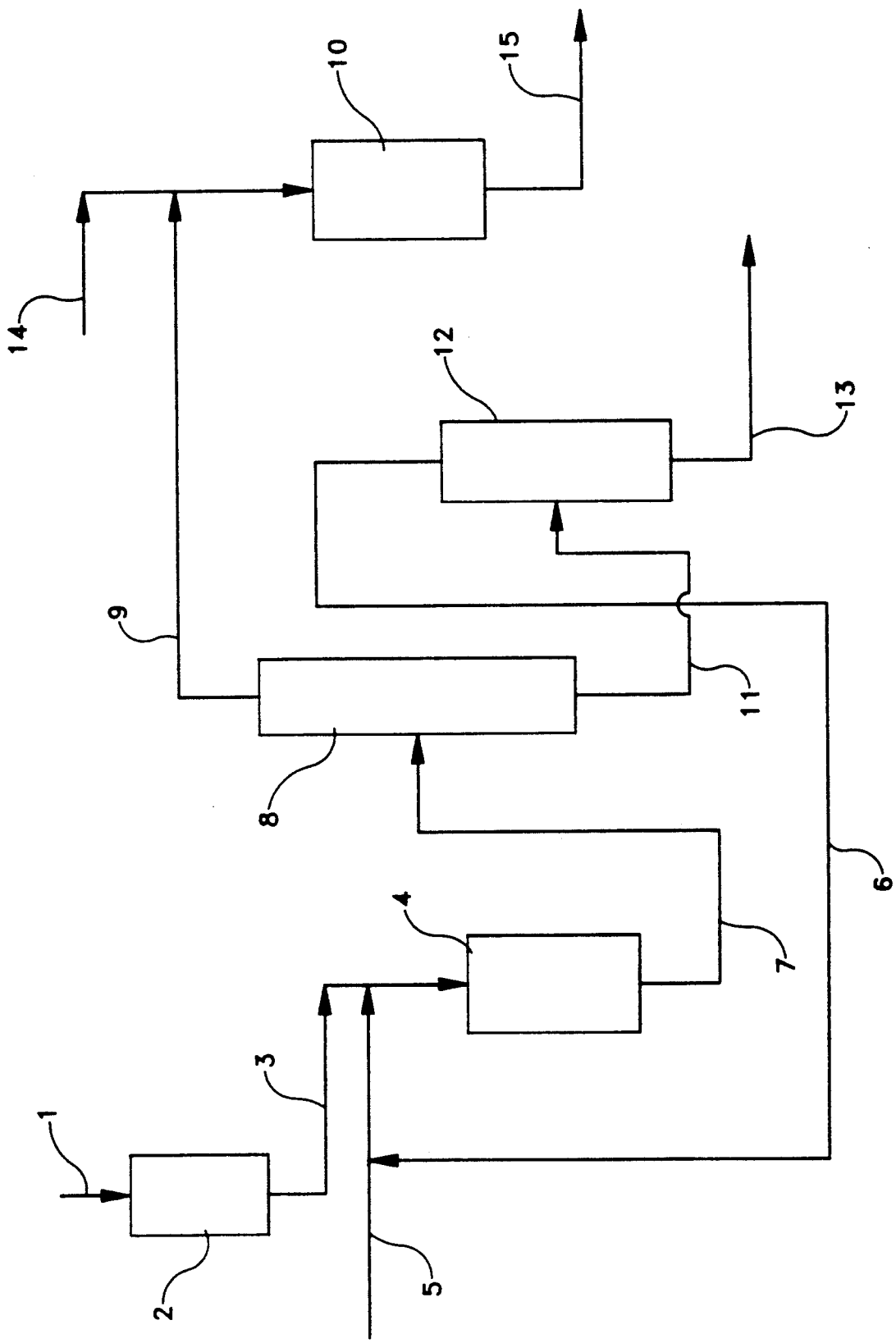

PREPARATION OF ALKYL TERTIARY BUTYL ETHER

BACKGROUND OF THE INVENTION

1. Field of the Invention

The present invention relates to a process for the preparation of methyl tertiary butyl ether (MTBE) or ethyl tertiary butyl ether (ETBE) wherein tertiary butyl alcohol (TBA) is reacted with methanol or ethanol and an effluent is formed which contains the water of reaction and at least 1 mol of methanol or ethanol for each 2 mols of MTBE or ETBE, the effluent is distilled to separate a mixture of ether and methanol or ethanol overhead from a bottoms which comprises the water of etherification, unreacted TBA and methanol or ethanol, and the overhead, preferably after distillation to reduce the methanol or ethanol content, is reacted with isobutylene to convert the lower alcohol contained therein to additional quantities of alkyl tertiary butyl ether.

2. Description of the Prior Art

MTBE and ETBE are important chemicals of commerce which have great utility, for example, as gasoline blending agents.

In the oxirane propylene oxide/TBA process there are produced both propylene oxide and tertiary butyl alcohol in exceedingly large quantities. It is advantageous to form MTBE and ETBE using the TBA formed in the above process.

Methods are known for the formation of MTBE and ETBE by reaction of the lower alcohol with isobutylene as well as by reaction of the alcohol with TBA.

A problem with the production of MTBE and ETBE by reaction of the lower alcohol and TBA is that water is a co-product of the reaction which is very difficult to separate from product ether since the two form an azeotrope which is expensive to break.

A problem with the production of MTBE or ETBE by first dehydrating TBA to isobutylene which is then reacted with the lower alcohol is that for liquid phase dehydrations, water is the heavy component which builds up, killing the reaction. Vapor phase dehydration is very costly in terms of capital and operating expense. The reaction of isobutylene with methanol or ethanol is highly exothermic, requiring large recirculation to remove heat of reaction, and the formation of the ether-lower alcohol azeotropes causes large recycle of ether to remove excess alcohol.

U.S. Pat. No. 4,918,244 shows the preparation of MTBE by reaction of TBA and methanol. The patent shows the distillation overhead of a MTBE and methanol mixture which is separated by gasoline and water extraction.

U.S. Pat. No. 5,099,072 shows the reaction of TBA and methanol to form MTBE.

U.S. Pat. No. 4,925,989 describes a process for preparing MTBE by feeding TBA, isobutylene and methanol to a combination reactor distillation tower.

U.S. Pat. No. 4,144,138 shows MTBE recovery from a reaction effluent containing MTBE, TBA, methanol and water by azeotropic distillation and extraction techniques.

U.S. Pat. No. 4,822,921 shows MTBE production by reaction of TBA and methanol.

European Publication 0 502 265 shows an integrated process for the production of MTBE involving, in part, reaction of isobutylene with methanol.

European Publication 0 502 651 shows MTBE production by reaction of TBA and methanol.

BRIEF DESCRIPTION OF THE INVENTION

In accordance with the present invention, TBA is reacted with methanol or ethanol to form respectively MTBE or ETBE as well as product water. The composition of the effluent is regulated such that the lower alcohol is contained therein in amount of at least 1 mol of lower alcohol per 2 mols ether, which helps to reduce undesirable products and which allows for separation of water from product ether by distillation. The effluent mixture is distilled to separate overhead a mixture of ether and lower alcohol from a bottoms product containing unreacted TBA, essentially all of the water of etherification, and the lower alcohol. The overhead product should contain at least one mol of lower alcohol for every 3 mols of ether. At such levels of lower alcohol concentration, water is separable from the ether even at low water concentrations. For example, the relative volatility, alpha, for water compared with MTBE is 1.8 in a mixture of 99 mols MTBE and 1 mol water. In a mixture of 81 mols MTBE, 18 mols methanol and 1 mol water, the alpha for water is 1.0 which does not allow water/MTBE separation. However, in a mixture of 69 mols MTBEL 30 mols methanol and 1 mol water, where the MTBE/methanol mol ratio is 2.3, the alpha for water is only 0.68 which will allow for water separation by distillation and producing an MTBE/methanol mixture as distillate. The mixture can be the MTBE/methanol azeotrope under adequate distillation conditions.

In the case of ETBE, water forms an azeotrope with ETBE at approximately 25 mol % water concentration. At lower concentrations of water, water is a light with respect to ETBE. However, even at low water concentrations, the presence of at least 1 mol ethanol per 2 mols ETBE makes water a separable heavy. The alpha for water with respect to ETBE is 0.68 for mixtures of 31 mols ETBE, 64.7 mols ethanol and 4.3 mols water and 0.53 for mixtures of 23 mols ETBE, 74 mols ethanol and 3 mols water, for example.

The overhead product from the water separation distillation, preferably after further distillation to separate the ether/lower alcohol azeotrope from excess lower alcohol, is contacted with isobutylene at conditions effective to convert the lower alcohol contained therein to MTBE or ETBE.

DESCRIPTION OF THE DRAWING

The attached drawing illustrates in schematic form practice of the invention.

DETAILED DESCRIPTION

Referring to the attached drawing, crude TBA is passed via line 1 to guard bed 2 wherein impurities such as acids and peroxidic materials are removed in accordance with known procedures.

Purified TBA passes via line 3 to etherification zone 4 wherein it is reacted with methanol or ethanol in accordance with known procedures to produce MTBE or ETBE, respectively. Fresh lower alcohol is introduced via line 5 and a recycle stream mainly comprised of TBA, lower alcohol and some water is introduced via line 6.

The etherification reaction in zone 4 is carried out at known conditions to produce MTBE or ETBE. It is important, in accordance with the invention, that the ether-containing product which is passed via line 7 to distillation zone 8 contain at least 1 mol lower alcohol for every 2 mols of ether contained therein, and preferably at least 1 mol lower alcohol for every mol of ether contained therein.

It is preferred to regulate the ratio of lower alcohol and TBA fed to etherification zone 4 and/or the degree of conversion in order that the reaction effluent from zone 4 contain at least 1 mol lower alcohol per 2 mols of ether. As a less desirable alternative, lower alcohol can be added to the effluent from zone 4 (not shown) in order to provide the minimum of at least 1 mol lower alcohol per 2 mols of ether.

The mixture comprised of lower alcohol, ether, TBA and water from zone 4 passes via line 7 to distillation zone 8 wherein the mixture is subjected to fractional distillation. An overhead stream consisting essentially of lower alcohol and ether is removed from zone 8 via line 9 and passes to etherification zone 10. Optionally, the overhead stream can be further distilled (not shown) to separate lower alcohol for recycle to zone 4 from a lower alcohol/ether azeotrope which passes to zone 10.

A bottoms stream consisting essentially of lower alcohol, TBA and water of etherification is removed from zone 8 via line 11 and passes to distillation zone 12 wherein an overhead stream consisting of lower alcohol and TBA and a small amount of water is recovered and recycled via line 6 to reaction zone 4. Bottoms from distillation zone 12 comprises the net water of etherification and is purged via line 13.

The lower alcohol/ether stream from zone 8 passes via line 9 to zone 10 wherein it is contacted with isobutylene introduced via line 14 under conditions effective to react the isobutylene and lower alcohol to form additional MTBE or ETBE. The product stream containing the ether formed both in zone 4 and in zone lo is recovered via line 15. This stream may be treated by known procedures to separate high purity product MTBE or ETBE from other components such as isobutylene and residual alcohols which can be recycled.

Essential to successful practice of the invention is the provision of the stated minimum amount of lower alcohol in the feed to distillation zone 8 in order that essentially all of the product MTBE or ETBE from reaction zone 4 can be separated overhead substantially free of water with substantially all of the water of etherification being rejected as a heavy in the bottoms from zone 8.

The reaction between methanol or ethanol and TBA is carried out in accordance with known procedures for the production of MTBE or ETBE. Generally, such known procedures involve the use of a solid acidic catalyst such as a sulfonic acid ion exchange resin as described, for example, in U.S. Pat. No. 4,918,244 or the use of acidic silica-alumina catalysts as described, for example, in U.S. Pat. No. 5,099,072. The reaction is conveniently carried out at temperatures ranging from about 20° C. to about 300° C. and pressures ranging from about atmospheric to about 5000 psig although these ranges are not critical.

Generally, mol ratios of methanol or ethanol to TBA ranging from about 10:1 to about 1:10 are suitable. Generally, however, it is preferred to use a slight excess of lower alcohol, for example, about 1.1 to about 3.0 mols of methanol or ethanol per mol of TBA.

The etherification reaction is most preferably carried out such that the effluent contains substantial amounts of lower alcohol, that is at least 1 mol and preferably at least 2 mols of methanol or ethanol per 2 mols of ether. The degree of conversion is conveniently regulated by appropriate control of the reaction parameters including temperature, pressure and residence time in the reaction zone. In the less desired case where, for example, TBA is employed in excess and the normal reaction effluent does not contain the designated minimum concentration of methanol or ethanol, the effluent composition can be adjusted by lower alcohol addition to provide the necessary concentration of methanol or ethanol which is essential for successful practice of the present invention.

The etherification effluent containing the designated minimum amount of reethanol or ethanol is distilled in accordance with conventional procedures in order to separate overhead a mixture of lower alcohol and ether which is substantially free of water. The presence of the designated amount of lower alcohol in the feed to this distillation effectively reduces the volatility of water of etherification in the feed such that the mixture of lower alcohol and ether can be separated as light overhead from the distillation zone with the water being separated in admixture with unreacted TBA and some lower alcohol as a high boiling fraction. As a result of this distillation, product ether in admixture with lower alcohol is conveniently separated from the water of etherification which otherwise is quite difficult to separate.

A key aspect of the present invention is the further reaction of the overhead lower alcohol and ether fraction with isobutylene in accordance with known and conventional procedures whereby the methanol or ethanol contained in the overhead mixture is effectively converted to supplemental quantities of MTBE or ETBE while avoiding the normal difficult and costly separation of lower alcohol and ether. The reaction of isobutylene with reethanol or ethanol is accomplished in accordance with known procedures, generally involving the use of a solid acidic catalyst such as a sulfonic acid ion exchange resin, the provision of temperatures generally ranging from about 20° C. to 300° C. and the use of pressures from atmospheric to about 5000 psig. It is advantageous to employ isobutylene slightly in excess of the stoichiometric amount necessary to react with the lower alcohol to form the corresponding ether,, for example, about 1.1 to about 1.5 mols isobutylene per mol of methanol or ethanol. Unreacted isobutylene is readily separated from product ether in accordance with known procedures.

Depending on the quantity of methanol or ethanol in the lower alcohol and ether mixture removed overhead from distillation zone 81 it is frequently advantageous to further distill this mixture in order to separate a lower alcohol/ether azeotrope from excess lower alcohol. The excess lower alcohol can be recycled to reaction with TBA and the azeotrope can be treated by reaction with isobutylene as above described.

The bottoms from distillation zone 8 comprised of lower alcohol, water and TBA is distilled in order to separate a lower alcohol, TBA and water fraction overhead, which fraction is conveniently recycled to the etherification reaction. A bottoms aqueous stream from this distillation represents a purge of the net water formed in the etherification.

Practice of the present invention has the outstanding advantage that costly and difficult separations are essentially avoided while at the same time the high capital and utilities required generally involved in the dehydration of TBA to isobutylene is minimized. Practice of the invention represents a significant economic advance of current technologies in the production of MTBE and ETBE, two very important commercial chemicals.

The following example illustrates the invention with reference to the attached drawing.

TBA in amount of 427 mols/hr. is introduced via line 1 to guard bed 2 which contains an adsorbent consisting of sodium and cobalt oxides on activated alumina or ion exchange resins in order to remove various impurities. The treated TBA passes via line 3 to etherification reactor 4 and also fed to this reactor is net reethanol via line 5 in amount of 1048 mols/hr. and a recycle stream via line 6 which comprises 372 mols/hr. of methanol, 166 mols/hr. of TBA and 142 mols/hr. of water. In reactor 4 the mixture is contacted with Amberlyst 15 resin at a temperature of 120° C. and a pressure of 120 psig in order to react methanol and TBA. The effluent from reactor 4 passes via line 7 to distillation zone The molar composition of this effluent is 46% reethanol, 8% TBA, 20% MTBE and 26% water.

Distillation zone 8 is a conventional fractional distillation column having 25 theoretical stages. An overhead stream comprised of 621 mols/hr. methanol and 427 mols/hr. MTBE is removed via line 9 at 73° C. and 30 psia. This stream passes to reactor 10 which is also packed with Amberlyst 15 wherein it is combined with 627 mols/hr. isobutylene which is introduced via line 14. Conditions in reactor 10 are 60° C., 300 psig at a feed rate (after combining the isobutylene) of 1.5 lbs. of combined feed per hour per lb. of dry resin for reaction of methanol and isobutylene. The effluent from reactor 10 is removed via line 15 and after separation of unreacted isobutylene and methanol (not shown) represents the 14TBE product of the process of this invention in amount of 1045 mols/hr.

A bottoms stream is removed from column 8 via line 11 at 101° C. and 34 psia and has a molar composition of 34% TBA, 15% methanol and 51% water. This mixture passes via line 11 to conventional fractional distillation zone 12 which is a distillation column having 20 theoretical stages. From column 12 an overhead stream comprised of 166 mols/hr. TBA, 372 mols/hr. methanol and 142 mols/hr. water is separated and recycled as above mentioned to reaction zone 4. A bottoms stream comprised of 421 mols/hr. water, and traces of methanol and TBA is purged via line 13.

We claim:

1. The process for the production of methyl tertiary butyl ether of ethyl tertiary butyl ether which comprises:
    a) reacting tertiary butyl alcohol with a lower alcohol selected from methanol or ethanol in an etherification zone and forming an etherification effluent containing lower alkyl tertiary butyl ether, water of reaction, and lower alcohol, the concentration of lower alcohol in said effluent being at least 1 mol lower alcohol per 2 mols lower alkyl tertiary butyl ether;
    b) passing the etherification effluent to a distillation zone and distilling the effluent from step a) to separate an overhead mixture of ether and lower alcohol substantially free of water from a bottoms comprised of tertiary butyl alcohol, lower alcohol and water; and
    c) reacting a lower alcohol/ether admixture from said overhead mixture with isobutylene in a second etherification zone to form lower alkyl tertiary butyl ether.

2. The process of claim 1 wherein the overhead mixture from step b) contains lower alcohol in excess of the lower alcohol/ether azeotropic composition and the excess lower alcohol is separated by distillation from the azeotropic composition.

3. The process of claim 1 wherein the effluent from step a) contains at least 1 mol lower alcohol per mol ether.

4. The process for the production of methyl tertiary butyl ether which comprises:
    a) reacting tertiary butyl alcohol with methanol in an etherification zone and forming an etherification effluent containing methyl tertiary butyl ether, water of reaction, and methanol, the concentration of methanol in said effluent being at least 1 mol methanol per 2 mols methyl tertiary butyl ether;
    b) passing the etherification effluent to a distillation zone and distilling the effluent from step a) to separate an overhead mixture of methyl tertiary butyl ether and methanol substantially free of water from a bottoms comprised of tertiary butyl alcohol, methanol and water; and
    c) reacting a methanol and ethyl tertiary butyl ether admixture from said overhead mixture with isobutylene in a second etherification zone to form methyl tertiary butyl ether.

5. The process for the production of ethyl tertiary butyl ether which comprises:
    a) reacting tertiary butyl alcohol with ethanol in an etherification zone and forming an effluent containing ethyl tertiary butyl ether, water of reaction, and ethanol, the concentration of ethanol in said effluent being at least 1 mol ethanol per 2 mols ethyl tertiary butyl ether;
    b) passing the etherification effluent to a distillation zone and distilling the effluent from step a) to separate an overhead mixture of ethyl tertiary butyl ether and ethanol substantially free of water from a bottoms comprised of tertiary butyl alcohol, ethanol and water; and
    c) reacting an ethanol and ethyl tertiary butyl ether admixture from said overhead mixture with isobutylene in a second etherification zone to form ethyl tertiary butyl ether.

* * * * *